United States Patent [19]

Haber et al.

[11] Patent Number: 5,647,845

[45] Date of Patent: Jul. 15, 1997

[54] GENERIC INTRAVENOUS INFUSION SYSTEM

[75] Inventors: Terry M. Haber, El Toro; William H. Smedley, Lake Elsinore; Clark B. Foster, Laguna Niguel, all of Calif.

[73] Assignee: Habley Medical Technology Corporation, Lake Forest, Calif.

[21] Appl. No.: 382,127

[22] Filed: Feb. 1, 1995

[51] Int. Cl.$^6$ ................................................ A61M 5/00
[52] U.S. Cl. ............................. 604/32; 604/403; 604/411
[58] Field of Search ............................. 604/30, 32, 403, 604/411, 412, 414, 905

[56] References Cited

U.S. PATENT DOCUMENTS

| | | | |
|---|---|---|---|
| 3,078,848 | 2/1963 | Milbert | 604/32 |
| 3,157,201 | 11/1964 | Littmann | 604/32 X |
| 3,411,534 | 11/1968 | Rose | 604/32 X |
| 3,780,736 | 12/1973 | Chen | 604/32 |
| 3,993,063 | 11/1976 | Larrabee | 604/414 X |
| 4,525,156 | 6/1985 | Benusa et al. | 604/32 X |
| 4,607,671 | 8/1986 | Aalto et al. | 604/412 X |
| 5,201,717 | 4/1993 | Wyatt et al. | 604/905 X |
| 5,238,582 | 8/1993 | Hori et al. | 604/403 X |
| 5,304,163 | 4/1994 | Bonnici et al. | 604/403 |
| 5,308,347 | 5/1994 | Sunago et al. | 604/411 X |
| 5,340,364 | 8/1994 | Ghelli et al. | 604/30 X |
| 5,411,359 | 5/1995 | Vaillancourt | 604/905 X |

FOREIGN PATENT DOCUMENTS

WO86/01712  8/1986  WIPO .................................. 604/411

*Primary Examiner*—Sam Rimell
*Attorney, Agent, or Firm*—Morland C. Fischer

[57] ABSTRACT

An economical, reliable and universal intravenous infusion system is disclosed which permits a customized or generic fluid or powder medication stored in a proprietary or conventional pharmaceutical vial to be mixed in solution with the fluid contents of an IV bag so that the mixture can be administered according to the needs of a patient via an IV fluid line having a drip chamber connected therein. Fluid communication between the IV bag and one of the IV fluid line and the pharmaceutical vial is selectively controlled by the position of a rotatable valve barrel in a fluid control valve. A universal vial receiving and docking receptacle that is uniquely and advantageously adapted to accept and carry pharmaceutical vials of different size moves through a hollow docking port from a first, as-packaged location, to a second location at which the vial is placed in fluid communication with the IV bag via the valve barrel at such time when the IV is to be administered.

20 Claims, 13 Drawing Sheets

GENERIC INTRAVENOUS INFUSION SYSTEM

BACKGROUND OF THE INVENTION

1. Field of the Invention

This invention relates to an economical, reliable and universal intravenous infusion system which permits a customized or generic fluid or powder medication stored in a proprietary or conventional pharmaceutical vial to be mixed in solution with the fluid contents of an IV bag so that the mixture can be administered according to the needs of a patient via an IV fluid line having a drip chamber connected therein.

2. Background Art

IV infusion systems have long been used to administer medication to a patient undergoing treatment. In general terms, an IV bag containing a low viscosity fluid hangs from a stand to supply medication, under the influence of gravity, to a patient via a flexible fluid line having a cannula at one end thereof to make a veni puncture. However, in one IV system, a proprietary pharmaceutical vial containing a customized or generic medication is interfaced with a proprietary IV bag. This arrangement results in increased cost for purchasing customized vials and IV bags from a limited number of manufacturers. Moreover, in some cases, the purchaser may be required to report confidential sales information to the manufacturer of such customized vials and bags as part of the purchase agreement.

In other IV systems, a stable pharmaceutical solution having an extended life span is produced by mixing and freezing the solution in the IV bag. The solution is maintained in a frozen state until an IV is administered to the patient. The foregoing method of increasing pharmaceutical life span requires the cost and inconvenience associated with the acquisition of freezing equipment and is limited to medication that is capable of being frozen without degradation. However, such medication may have to be discarded in the event of a premature thaw prior to administering the IV.

SUMMARY OF THE INVENTION

This invention relates to a generic IV infusion system to be coupled between an IV bag and an IV fluid line having a drip chamber connected therein so that both customized and generic pharmaceuticals stored in both proprietary and conventional medication/pharmaceutical vials can be administered in solution to a patient. The IV infusion system includes the interconnection of a fluid control valve, a universal vial receiving and docking receptacle to accept and carry medication/pharmaceutical vials of different size and a vial limiting end cap affixed to the distal end of the receptacle.

The distal end of the fluid control valve includes a rotatable valve barrel having fluid distribution paths extending therethrough. The position of the valve barrel and the ability of the valve barrel to distribute fluid is controlled by a mode selection knob. Projecting distally from the fluid control valve and adapted to communicate with the fluid distribution paths of the valve barrel is an administration port cannula. Projecting proximally from the fluid control valve and adapted to communicate with the fluid distribution paths of the valve barrel is a vial cannula. Projecting laterally from the fluid control valve and adapted to communicate with the fluid distribution paths of the valve barrel is an IV drip chamber tube. The proximal end of the fluid control valve forms a hollow, cylindrical two-stage docking port through which the vial receiving and docking receptacle is moved during two stages of operation. To this end, a locking tab which projects from the end cap of the vial receiving and docking receptacle is pushed through a track formed in a side of the fluid control valve in order to move the vial receptacle and a medication/pharmaceutical vial carried thereby distally through the docking port during each stage of operation.

The universal vial receiving and docking receptacle includes a hollow open-ended body having a series of flexible retaining arms spaced evenly around and projecting radially inward therefrom. Each retaining arm terminates at a relatively wide centering finger, and the centering fingers of the respective retaining arms are separated from one another to define an annular web within which to accept and retain the vial. An incoming vial of relatively small diameter applies pushing forces against the centering fingers which in turn cause the flexible retaining arms to bend. An incoming vial of relatively large diameter applies pushing forces directly against the retaining arms causing the arms to bend. When the end cap of the incoming vial moves past the retaining arms, the potential energy stored therein causes the centering fingers to snap around the neck of the vial to reliably attach the vial to the vial receiving and docking receptacle so as to be moved distally therewith through the docking port of the fluid control valve.

In the as-packaged condition of the generic intravenous infusion system, a medication/pharmaceutical vial having the desired fluid or powder medication to treat a patient is located in the vial receiving and docking receptacle. The locking tab projecting from the end cap of the vial receiving and docking receptacle is moved into a detent formed in the track of the fluid control valve to position the vial carried by the vial receptacle in spaced coaxial alignment with the vial cannula. Next, an IV bag is hung from an IV stand and the administration port cannula is located within but does not yet pierce the existing administration port of the IV bag. Similarly, the IV drip chamber tube is coupled to an IV fluid line having a drip chamber connected therein. During the foregoing, the mode selection knob is rotated to the off position to block the distribution of fluid from the IV bag by way of the valve barrel of the fluid control valve.

When it is time to administer an IV, the locking tab projecting form the end cap of the vial receiving and docking receptacle is pushed distally and completely through the track in the fluid control valve. Accordingly, the vial receptacle and the medication/pharmaceutical vial carried thereby are correspondingly moved distally through the docking port of the fluid control valve until the vial cannula penetrates the septum of the vial. The administration port of the IV bag is now pierced by the administration port cannula. The mode selection knob is rotated from the off position to the medication mixing position, whereby a fluid distribution channel is opened through the valve barrel of the fluid control valve between the IV bag and the vial so that the fluid contents of the bag can be mixed under the influence of gravity with the medication stored in the vial. The vial is then momentarily raised above the IV bag to return the mixture of medication and fluid to the bag.

Lastly, the mode selection knob is rotated from the pharmaceutical mixing position to the patient infusing position, whereby a fluid distribution channel is opened through the valve barrel of the fluid control valve between the IV bag and the IV drip chamber tube so that the fluid contents of the IV bag and the medication mixed in solution therewith can be delivered to the patient under the influence of gravity via the IV fluid line. Once the patient IV is completed, the used IV bag and the generic IV infusion system coupled thereto are simply and conveniently discarded.

DETAILED DESCRIPTION

Figure 1:
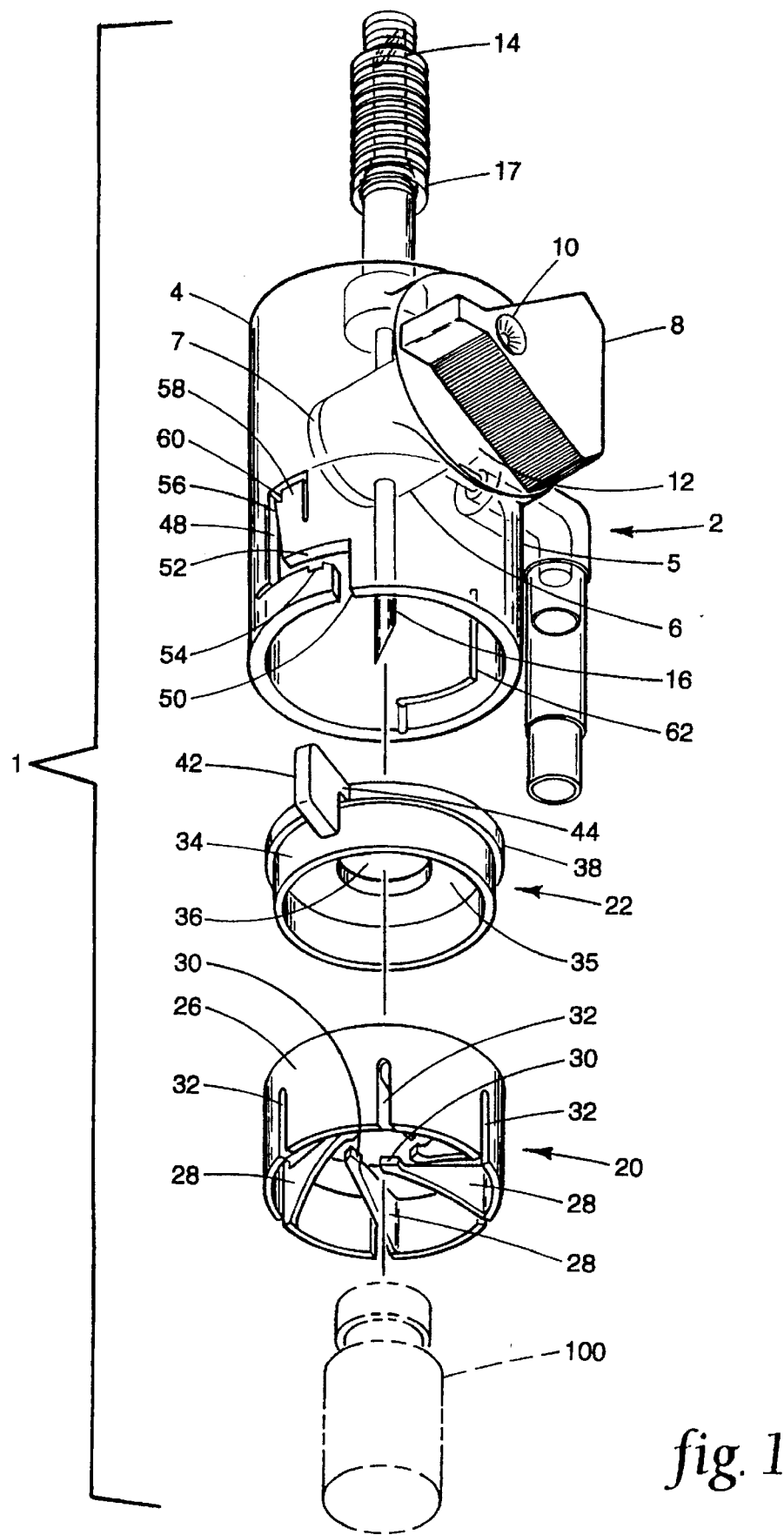
FIG. 1 is an exploded view of the generic intravenous infusion system which forms the present invention.

The generic intravenous infusion system 1 which forms the present invention is described while initially referring to FIG. 1 of the drawings. As will be described in greater detail hereinafter, the intravenous infusion system 1 is coupled to a conventional IV bag whereby the fluid contents of the bag can be mixed with the contents of a conventional or proprietary medication/pharmaceutical vial so that the mixture can be administered to a patient via an IV fluid line according to the particular needs of the patient. The intravenous infusion system 1 includes the interconnection of a fluid control valve 2, a universal vial receiving and docking receptacle 20, and a vial limiting end cap 22 affixed to the distal end of receiving and docking receptacle 20.

Figure 8:
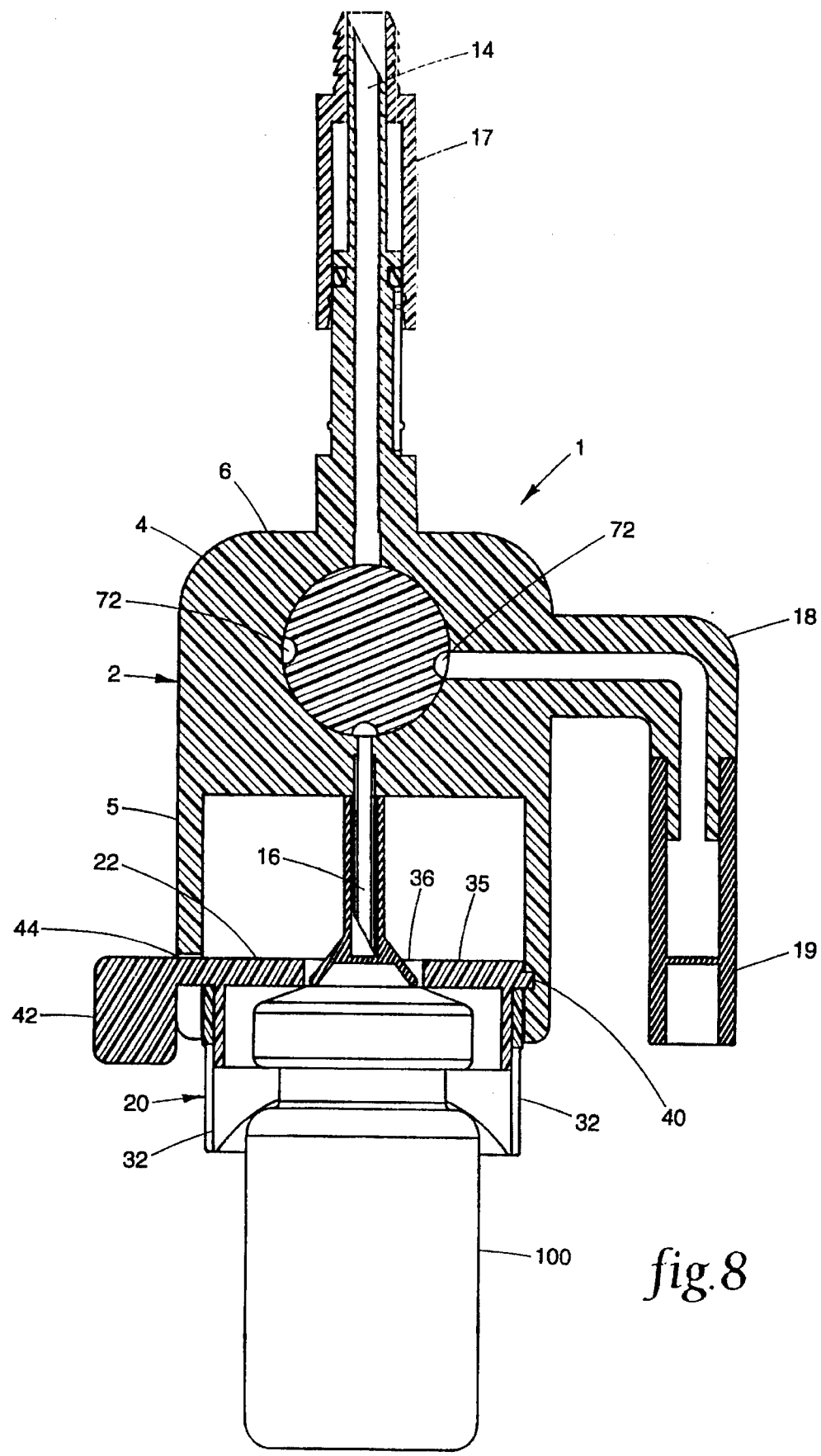
FIG. 8 is a cross-section of the generic intravenous infusion system in the assembled, as-packaged configuration with a pharmaceutical vial attached to the universal receiving and docking receptacle.

The fluid control valve 2 of infusion system 1 includes a cylindrical housing 4 that is preferably manufactured from a transparent, chemically resistant thermoplastic polymer. As is best shown in FIG. 8, the distal end of housing 4 is of solid cross section while the proximal end is hollow to form a two-stage docking port 5 within which to accommodate the vial receiving and docking receptacle 20. Located within the distal end of housing 4 is a rotatable valve barrel 6. The rotatable valve barrel 6 is of solid cross section except for a series of fluid distribution paths 72 and a hollow fluid collection chamber 7 (best shown in FIGS. 8, 12 and 14) that can be selectively oriented to permit communication between the IV bag and the medication/pharmaceutical vial or the fluid IV line depending upon the position to which the valve barrel 6 is rotated within housing 4.

To this end, the valve barrel 6 of fluid control valve 2 is rotated relative to housing 4 by means of a mode selection knob 8. As will be described in greater detail hereinafter, and once the fluid control valve 2 has been coupled to an IV bag, the mode selection knob 8 is rotated by a health care worker to cause a corresponding rotation of the valve barrel 6 from the off position (as shown in FIGS. 1 and 8–10) to a pharmaceutical mixing position (shown in FIGS. 11 and 12) and then to a patient infusing position (shown in FIGS. 13 and 14). An optional window 10 may be formed through the mode selection knob 8 to enable a health care worker to easily and visibly identify the particular position to which knob 8 has been rotated. For example, if the mode selection knob 8 is rotated around a flat face 12 at one side of casing 4 and the flat face 12 is provided with adjacent areas of different color, the particular color that is visible to the health care worker through window 10 will verify the position of knob 8 and the direction in which fluid will flow through the fluid distribution paths of valve barrel 6.

Projecting distally through the housing 4 of fluid control valve 2 and communicating at a first end thereof with the valve barrel 6 is a hollow administration port cannula 14. Projecting proximally from the housing 4 of valve 2 and communicating at a first end thereof with the valve barrel 6 is a hollow vial cannula 16. The opposite ends of the cannulas 14 and 16 located farthest from the valve barrel 6 terminate with sharp tips that are adapted to pierce plastic and rubber. A flexible coupling sleeve 17 surrounds the administration port cannula 14 and is collapsible therealong. The proximal end of the coupling sleeve 17 is ribbed to facilitate manipulation (i.e. compression) thereof by a health care worker. The distal end of coupling sleeve 17 is relatively narrow to establish a reliable fluid-tight attachment to the usual IV administration port of a conventional IV bag.

Projecting laterally through the housing 4 of fluid control valve 2 and communicating at a first end thereof with the valve barrel 6 is an IV drip chamber tube (designated 18 and best shown in FIG. 8). The opposite end of tube 18 turns distally and terminates at a fluid port 19 that is adapted to be mated to a conventional IV fluid line (designated 82 in FIGS. 12 and 14).

The two-stage docking port 5 at the proximal end of the housing 4 of fluid control valve 2 is now described while continuing to refer to FIG. 1. Docking port 5 has a track 48 formed in one side thereof in which to receive the neck 44 of a locking tab 42 projecting from the vial limiting end cap 22. As will soon be described, the neck 44 of locking tab 42 is adapted to ride through track 48 so that a health care worker can selectively control the axial (i.e. distal) displacement of the vial receiving and docking receptacle 20 through the docking port 5 of housing 4 at each of two successive stages of operation of the intravenous infusion system 1.

More particularly, the track 48 formed in the two-stage docking port 5 of housing 4 includes an axial inlet slot 50 at the proximal end thereof to receive the neck 44 of the locking tab 42 of end cap 22. Inlet slot 50 communicates with a short circumferentially extending timing slot 52. A detent 54 is formed in timing slot 52 for the purpose of retaining the locking tab 42 of end cap 22 and the vial receiving and docking receptacle 20 in the as-packaged position (of FIG. 6) so as to avoid an axial displacement of receptacle 20 (and a medication/pharmaceutical vial carried thereby) relative to housing 4. An axially extending bayonet slot 56 communicates with the timing slot 52 through which the neck 44 of locking tab 42 of end cap 22 will be moved by a health care worker when it is desirable to cause a corresponding axial (i.e. distal) displacement of the vial receiving and docking receptacle 20 and the vial carried thereby. The track 48 turns back from the bayonet slot 56 towards the proximal end of the docking port 5 so as to define a flexible lock catch 58 having a small recess 60 in which to engage and retain the neck 44 of locking tab 42 of end cap 22 and thereby prevent a proximal relocation of the vial receiving and docking receptacle 20 through docking port 5 after the locking tab 42 has been moved completely and distally through track 48 (as shown in FIG. 7).

A cam track 62 is formed in the docking port 5 of housing 4 opposite track 48. Cam track 62 includes a series of slots that mirror the opposing track 48. The cam track 62 is positioned to receive a tracking pin (designated 40 in FIG. 8) which projects from the end cap 22 opposite locking tab 42. Accordingly, pin 40 will ride through cam track 62 and thereby stabilize the axial (i.e. distal) displacement of the vial receiving and docking receptacle 20 through docking port 5 as locking tab 42 is moved through the opposite track 48.

Figure 2A:
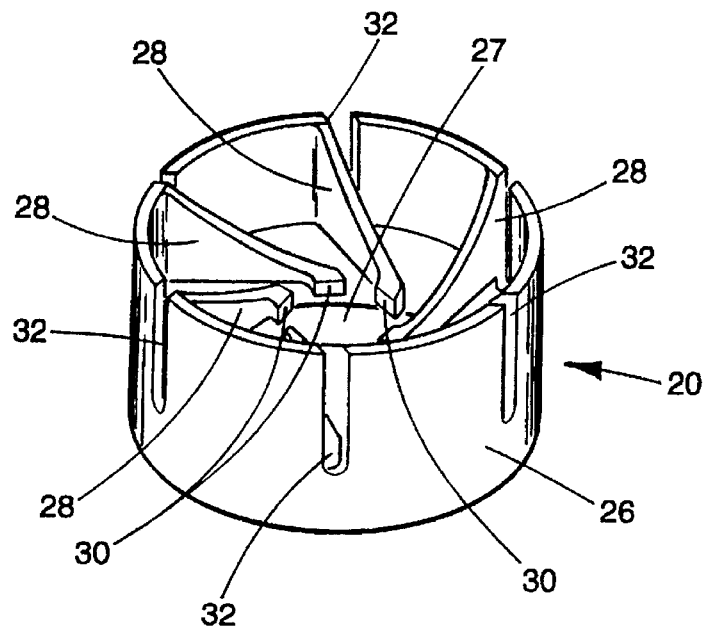
FIG. 2a is a perspective view of the universal vial receiving and docking receptacle which is a part of the intravenous infusion system of FIG. 1.

The details of the universal vial receiving and docking receptacle 20 are described while referring concurrently to FIGS. 1 and 2a of the drawings. By virtue of the vial receiving and docking receptacle 20, the intravenous infusion system 1 of this invention is advantageously and uniquely adapted to accept any commercially available or proprietary medication/pharmaceutical vial (shown in phantom lines and designated 100 in FIG. 1) regardless of diameter and without requiring that inefficient and time-consuming changes first be made to the system. Receptacle 20 includes a cylindrical body 26 that is manufactured from a resilient (e.g. plastic) material. Both the proximal and distal ends of body 26 are open to receive an incoming vial 100 therethrough. A plurality of flexible retaining arms 28 are evenly spaced around and project radially inward from the cylindrical body 26. Each retaining arm 28 terminates at a relatively wide centering finger 30. The centering fingers 30 at the radially inner-most ends of the retaining arms 28 are spaced relative to one another to form an annular web within which to accept the incoming vial 100.

As will be disclosed in greater detail hereinafter when referring to FIGS. 4 and 5, the retaining arms 28 of receptacle 20 are adapted to accommodate and support large diameter vials and the centering fingers 30 of arms 28 are adapted to accommodate and support small diameter vials. However, the ability of receptacle 20 to accommodate and support both conventional and proprietary medication/pharmaceutical vials of varying diameter is dependent upon the flexibility of the retaining arms 28 and the corresponding ability of arms 28 to bend and rotate slightly. To this end, a series of evenly spaced, longitudinally extending slots 32 are formed in the body 26 of receptacle 20 to enhance the ability of retaining arms 28 to flex in response to a mechanical pushing force applied thereagainst by the incoming vial 100 moving through the body 26.

As is best shown in FIG. 1, the vial limiting end cap 22 includes a cylindrical body 34. The proximal end of body 34 is open and the distal end 35 is closed, except for an access opening 36 extending therethrough. The partially closed distal end 35 of end cap 22 functions as a stop to limit the axial (i.e. distal) displacement of a medication/pharmaceutical vial 100 that is carried by the vial receiving and docking receptacle 20 until such time that a health care worker moves end cap 22 and the receiving and docking receptacle 20 affixed thereto through the docking port 5 at the proximal end of housing 4 of fluid control valve 2.

An annular lip 38 surrounds the distal end of body 34. The previously described tracking pin (designated 40 in FIG. 8) and the locking tab 42 project outwardly from the end cap 22 at opposite sides of the lip 38. As was also previously described, the locking tab 42 is joined to the lip 38 by a relatively narrow neck 44 that is adapted to ride through the track 48 in the two-stage docking port 5 of the housing 4 of fluid control valve 2.

Figure 2B:
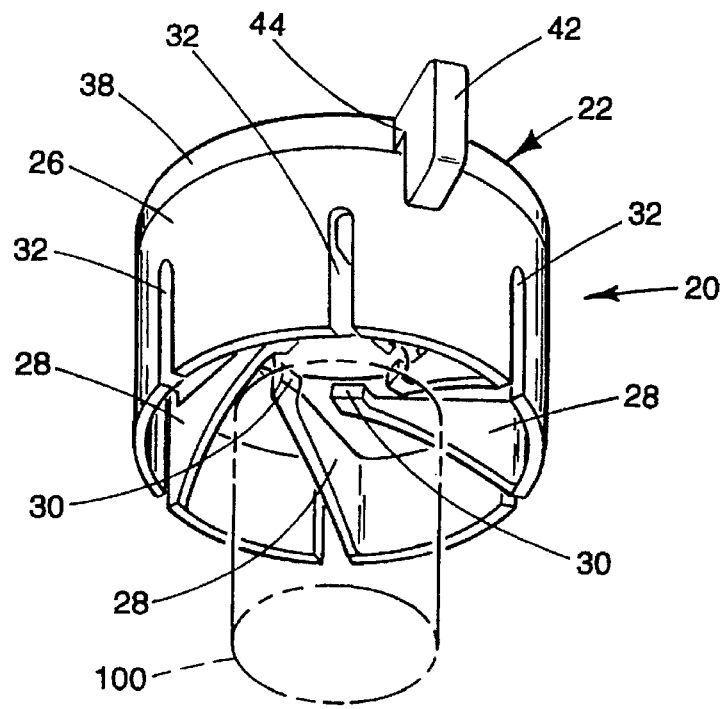
FIG. 2b is a perspective view showing the vial receiving and docking receptacle of FIG. 2a in the as-packaged condition having a vial limiting end cap connected across the distal end thereof and a pharmaceutical vial attached at the proximal end thereof.

In the assembled as-packaged configuration of intravenous infusion system 1, the cylindrical body 26 of the vial receiving and docking receptacle 20 is sized to surround the cylindrical body 34 of the vial limiting end cap 22 so that the distal end of body 26 is received against the annular lip 38. Accordingly, and as is best shown in FIG. 2b, the receptacle 20 and end cap 22 are mated together so that the access opening 36 through the distal end wall 35 of end cap 22 will be positioned in spaced parallel alignment with the septum of a medication/pharmaceutical vial 100 carried by receptacle 20.

Although the vial receiving and docking receptacle 20 and the vial limiting end cap 22 are shown in FIG. 1 as being separate, it is to be understood that during manufacture, the end cap 22 may be molded or sonically welded to the distal end of receptacle 20 to form an integral, one-piece vial receptacle. What is more, the two-stage docking port 5 at the proximal end of the housing 4 of fluid control valve 2 is sized to accommodate the distal movement therethrough of the vial receiving and docking receptacle 20 and the vial limiting end cap 22 connected thereto whereby to advance a medication/pharmaceutical vial 100 carried by receptacle 20 towards the vial cannula 16 within housing 4.

Figure 3:
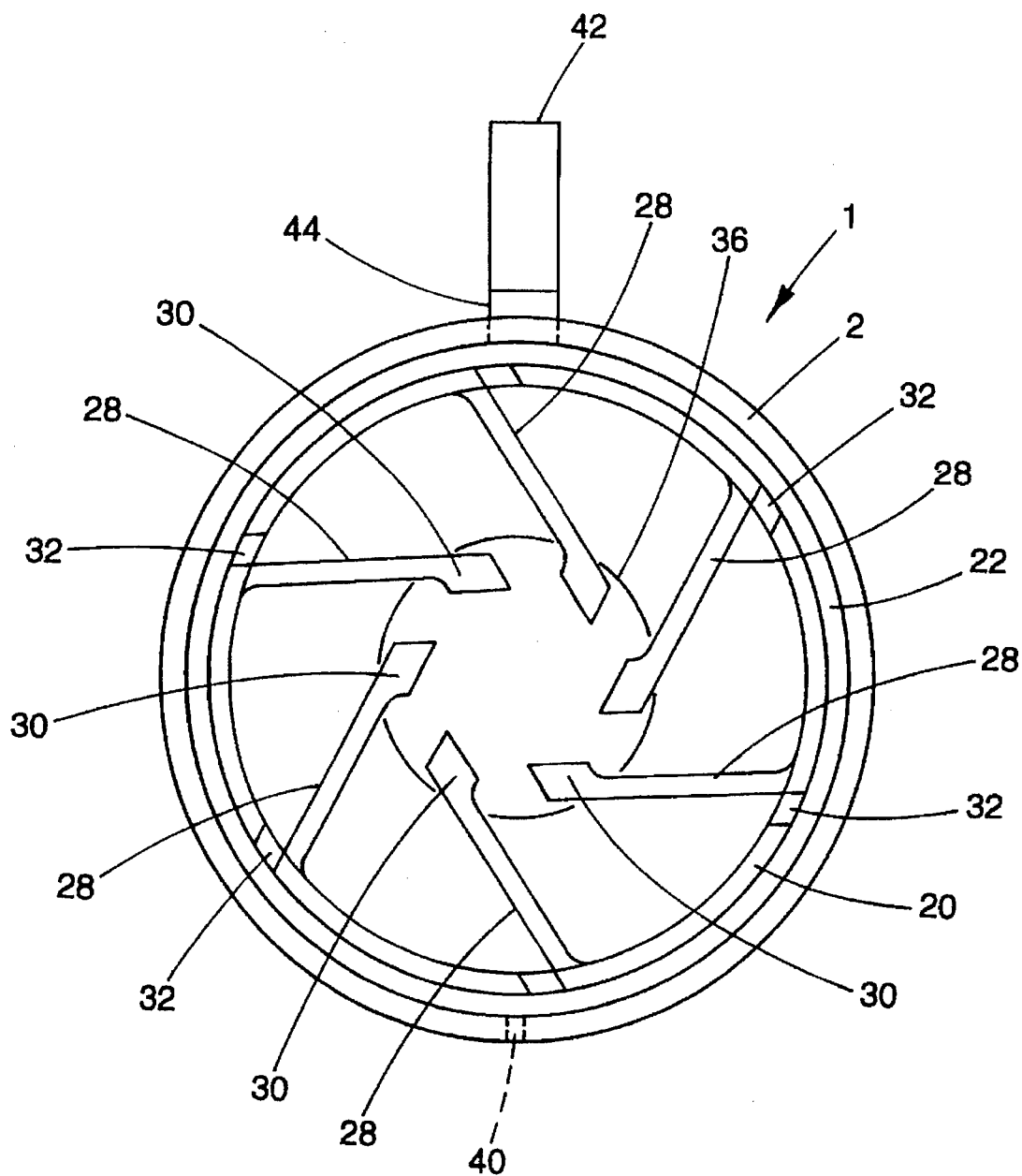
FIG. 3 shows the intravenous infusion system of FIG. 1 assembled in the as-packaged configuration.
Figure 4:
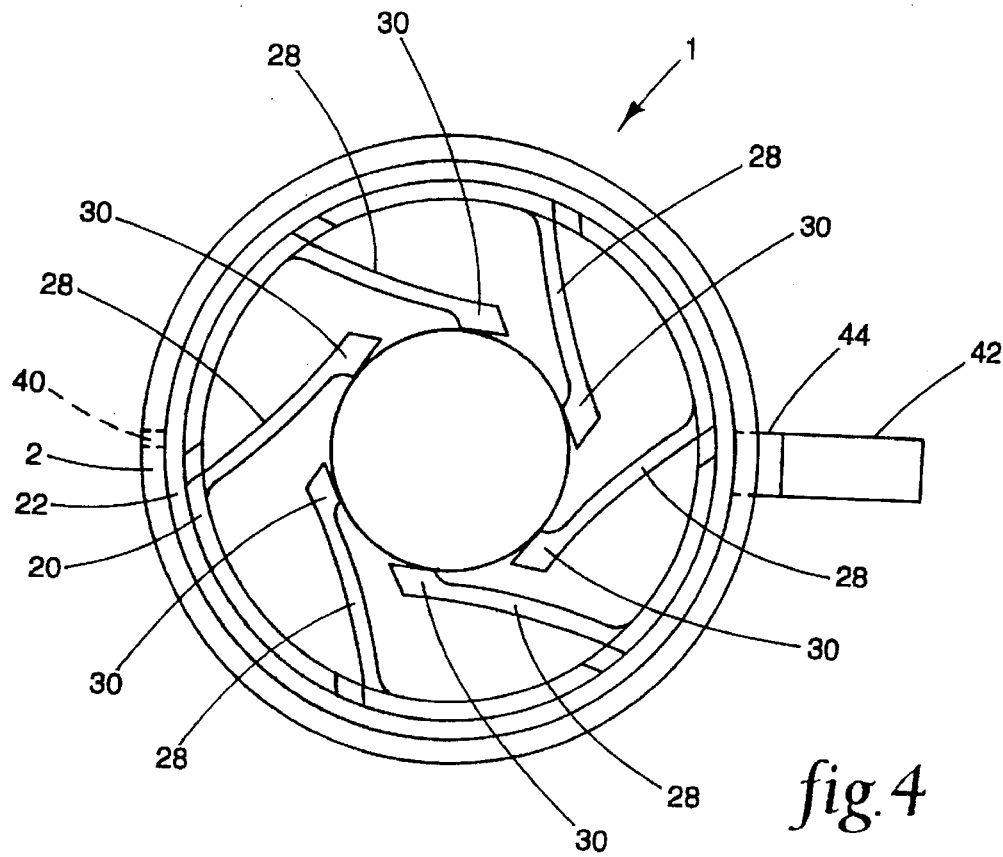
FIGS. 4 and 5 illustrate the manner in which the universal vial receiving and docking receptacle of the intravenous infusion system of FIG. 3 is adapted to receive pharmaceutical vials of both small and large diameter.
Figure 5:
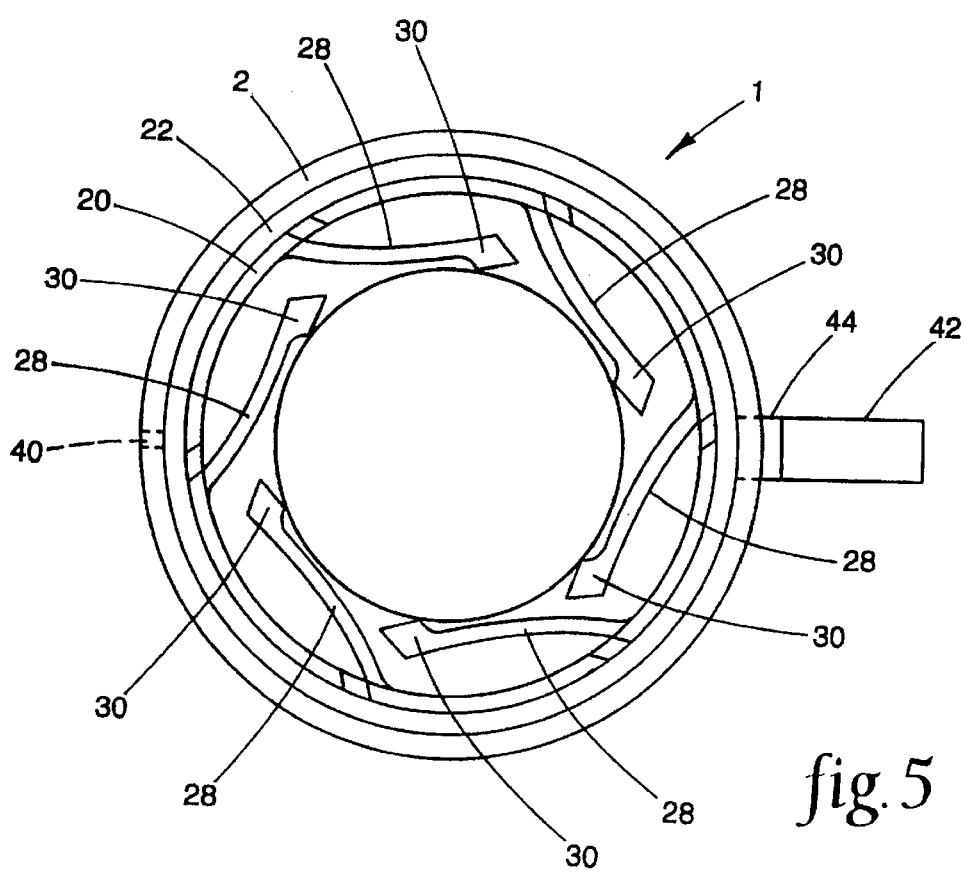

FIGS. 3–5 of the drawings illustrate the manner in which the universal vial receiving and docking receptacle 20 of the intravenous infusion system 1 is uniquely and advantageously adapted to accept and carry medication/pharmaceutical vials of different sizes after the fluid control valve 2, end cap 22 and receptacle 20 have been assembled in the as-packaged condition of FIG. 3. In the as-packaged configuration, the vial receiving and docking receptacle 20 is devoid of any vial. In this case, no bending stresses are applied to the resilient retaining arms 27 of receptacle 20, and such retaining arms remain unflexed.

In FIG. 4, the vial receiving and docking receptacle 20 of the intravenous system 1 is shown accepting a distally incoming 5 medication/pharmaceutical vial 64 (in the manner shown by phantom lines of FIG. 1) of relatively small (e.g. 10 mm) diameter. In this case, the end cap of the incoming vial 64 engages the centering fingers 30 and applies bending forces thereagainst. The bending forces applied to fingers 30 cause the respective retaining arms 28 to flex and rotate slightly away from the incoming vial 64. Once the end cap of vial 64 is moved axially and distally past the centering fingers 30, the potential energy stored by the now flexed retaining arms 28 will cause the arms to rotate towards the vial 64, whereby centering fingers 30 will snap around the relatively narrow neck of the vial 64 so that the vial is securely mated to receptacle 20 and centered with respect to the access opening 36 through end cap 22.

In FIG. 5, the vial receiving and docking receptacle 20 is shown accepting a distally incoming medication/pharmaceutical vial 66 of relatively large (e.g. 20 mm) diameter. In this case, the end cap of incoming vial 66 will engage the retaining arms 28 to apply bending forces directly thereagainst, whereby to cause the retaining arms 28 to flex and rotate slightly away from the incoming vial 66. Once the end cap of vial 66 is moved axially and distally past the retaining arms 28, the potential energy stored by the now flexed arms 28 will cause the arms to rotate towards the vial 66, whereby the centering fingers 30 will snap around the neck of vial 66 so that the vial is securely mated to receptacle 20 and centered with respect to the access opening 36 through end cap 22.

Figure 6:
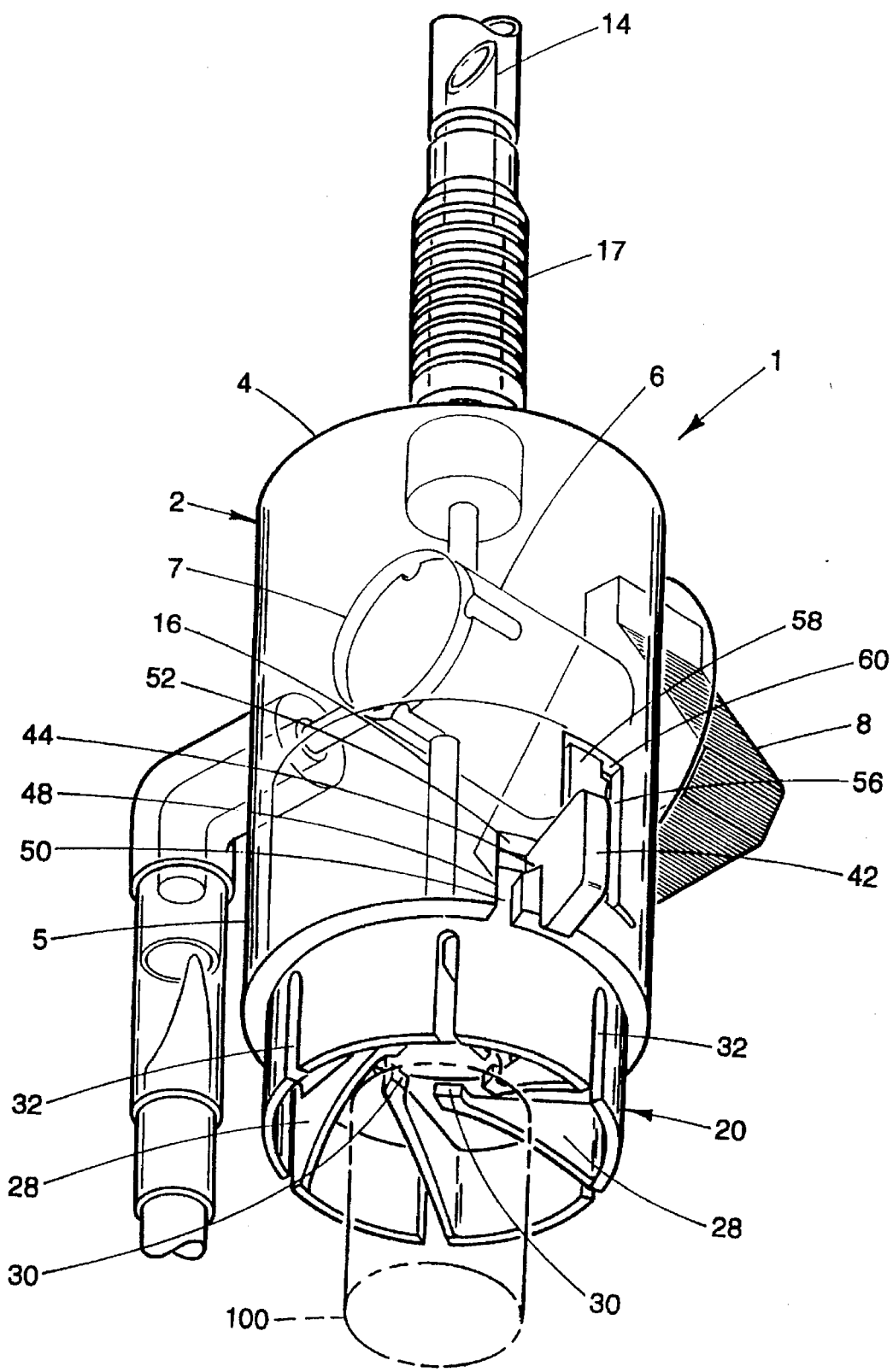
FIG. 6 shows the intravenous infusion system in the assembled, as-packaged configuration during a first stage of operation after a pharmaceutical vial has been attached therein.
Figure 7:
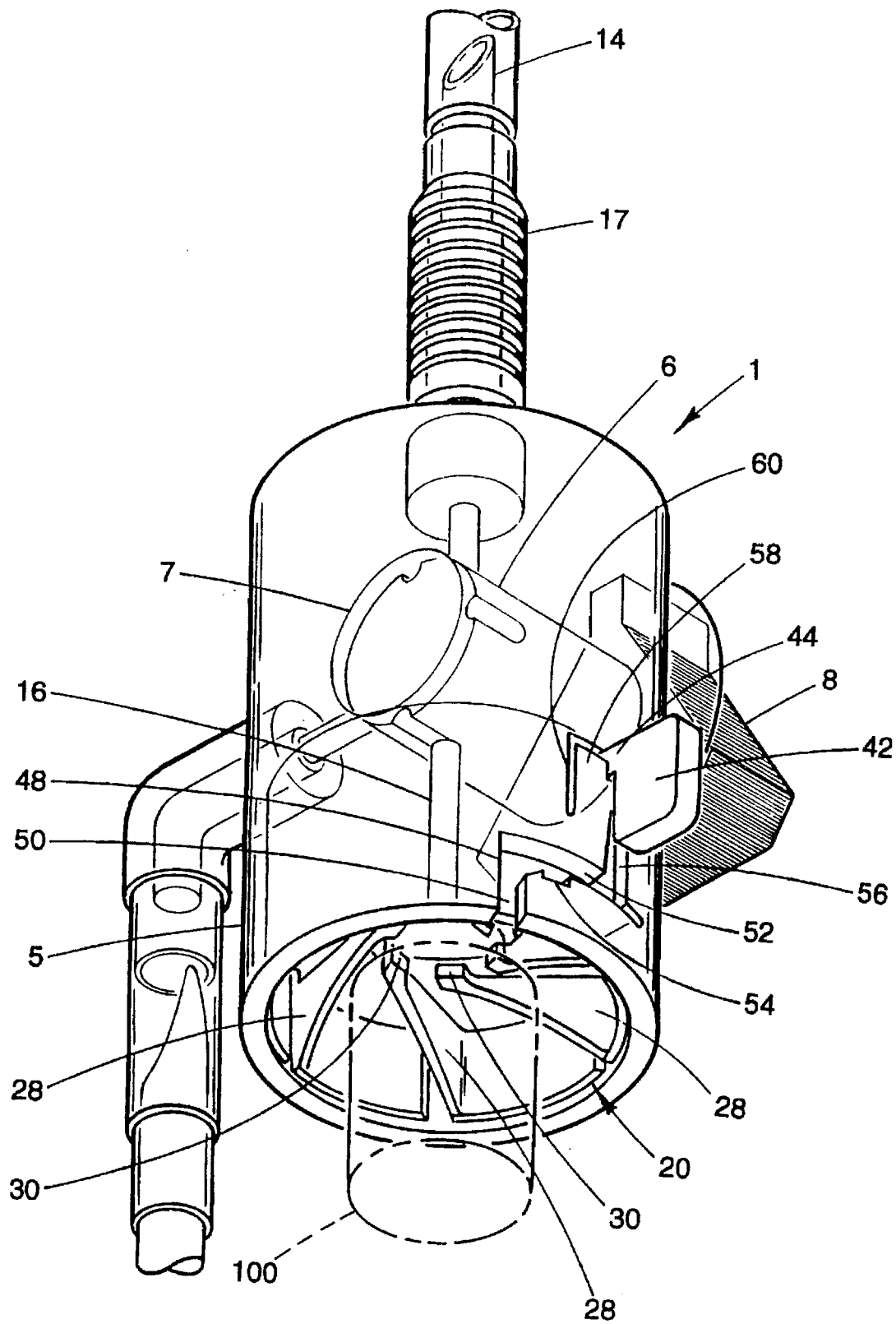
FIG. 7 shows the intravenous infusion system of FIG. 6 during a second stage of operation when an IV is to be administered to a patient.

FIGS. 6 and 7 of the drawings describe the steps by which a health care worker moves the universal vial receiving and docking receptacle 20 of the intravenous infusion system 1 relative to the two-stage docking port 5 of the fluid control valve 2 so that a medication/pharmaceutical vial 100 that is carried by receptacle 20 can be moved axially and distally through docking port 5. In FIG. 6, with the infusion system 1 shown in the as-packaged condition, a pharmacist or other health care worker first attaches the vial 100 to the vial receiving and docking receptacle 20 in the manner previously described when referring to FIGS. 4 and 5. Vial 100 may be of any conventional or proprietary size and contain any customized or generic liquid or powder medication that is to be administered to a patient in solution via a flexible IV fluid line.

In the as-packaged condition of FIG. 6, receptacle 20 is located at the proximal end of the docking port 5 of fluid control valve 2 such that the neck 44 of the locking tab 42 is moved axially through the inlet slot 50 and circumferentially through the timing slot 52 of the track 48 formed in the docking port 5 until the neck 44 is received by detent 54 (of FIG. 7). The locking engagement of the neck 44 of locking tab 42 within detent 54 prevents any unintentional distal displacement of the vial receiving and docking receptacle 20 relative to docking port 5 prior to the time that the medication stored in vial 100 is to be administered to the patient with an IV.

In order to advance the vial receiving and docking receptacle 20 and the vial 100 carried thereby axially and distally through the docking port 5 when the medication stored in the vial 100 is to be administered to the patient, a nurse or other health care worker who is in charge of administering an IV moves the neck 44 of locking tab 42 out of the detent 54 and through the track 48 in the docking port 5. That is to say, and as is best shown in FIG. 7, the locking tab 42 is moved so that the neck 44 first rides circumferentially through timing slot 52 and then distally through bayonet slot 56. When the locking tab 42 reaches the end of its travel along track 48 and receptacle 20 is moved distally and completely through docking port 5, the neck 44 will be received by and held within the recess 60 formed in the lock catch 58. Accordingly, the lock catch 58 is flexed slightly until the neck 44 is captured by recess 60 in order to to block the retraction of locking tab 42 through track 48 and prevent the proximal relocation through the docking port 5 of the vial receiving and docking receptacle 20 as well as the vial 100 carried thereby.

Figure 9:
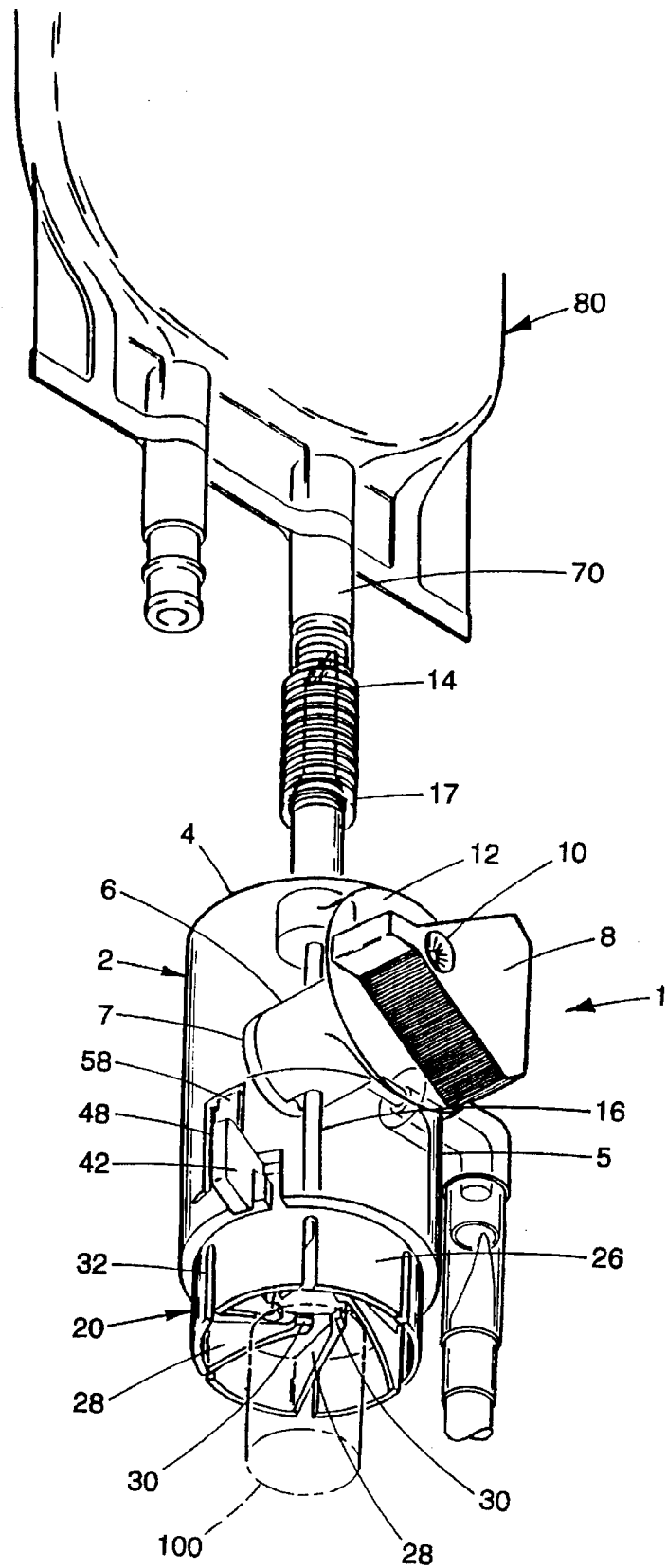
FIGS. 9 and 10 show the intravenous infusion system in the as-packaged condition coupled to a conventional IV bag with a mode selection knob rotated to the off position to prevent the distribution of fluid from the IV bag.
Figure 10:
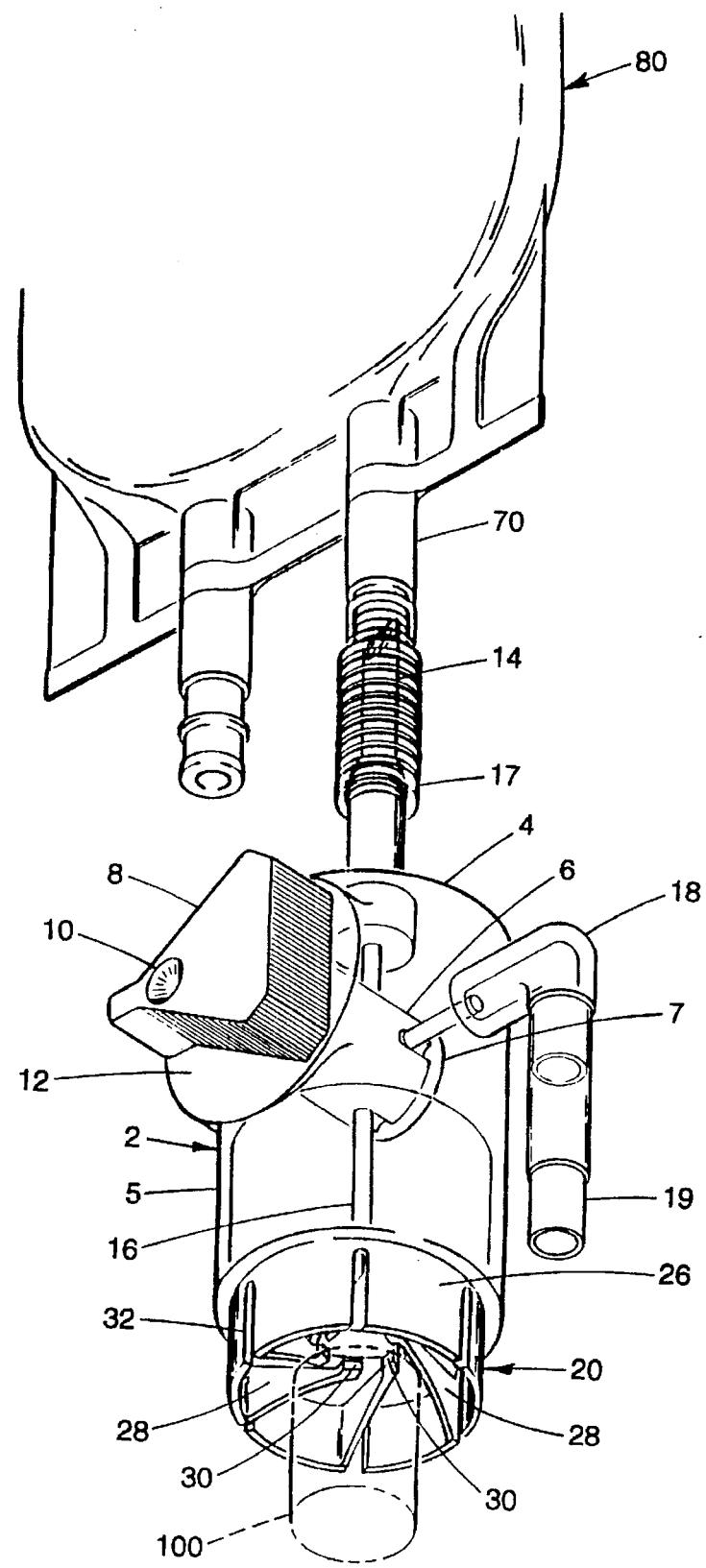

The operation of the generic intravenous infusion system 1 of this invention is now described in each of the off, pharmaceutical mixing and patient infusing positions of the mode selection knob 8 of fluid control valve 2. Referring first to FIGS. 8–10 of the drawings, the intravenous infusion system 1 is shown in the as-packaged condition, but after a pharmacist has attached a medication/pharmaceutical vial 100 to the universal vial receiving and docking receptacle 20 in the manner described while referring previously to FIGS. 4 and 5. What is more, the mode selection knob 8 is rotated to the left-most or off position. In the as-packaged condition of infusion system 1, the narrow end of the coupling sleeve 17 surrounding the administration port cannula 14 is coupled to the existing administration port 70 of an IV bag 80 that has been hung from an IV stand (not shown). However, with mode selection knob 8 rotated to the off position of FIGS. 8–10, the administration port cannula 14 does not pierce through the administration port 70 so that there is no fluid communication between the IV bag 80 and the intravenous system 1. Moreover, the drip chamber tube 18 is coupled to an IV fluid line (not shown) having a well known drip chamber connected therein.

As was also previously described when referring to FIG. 6, the nurse in charge of IV administration moves the vial receiving and docking receptacle 20 to the proximal end of the two-stage docking port 5 of the fluid control valve 2. In the first of the two stages, and prior to the administration of an IV, the locking tab 42 projecting from end cap 22 is manipulated so that the neck 44 of locking tab 42 rides through the inlet slot 50 and the timing slot 52 of the track 48 in docking port 5 until the neck 44 is received by detent 54. With the neck 44 of locking tab 42 located in detent 54, no further axial (i.e. distal) displacement of the receiving and docking receptacle 20 through docking port 5 can occur, whereby the septum of the medication/pharmaceutical vial 100 carried by vial receptacle 20 is held in spaced coaxial alignment with the vial cannula 16 below the access opening 36 through vial limiting end cap 22 (best shown in FIG. 8).

As is also best shown in FIG. 8, with the mode selection knob 8 rotated to the off position, the valve barrel 6 within housing 4 of fluid control valve 2 is correspondingly positioned so that the fluid distribution paths 72 thereof are oriented to prevent communication between the IV bag 80 and either of the medication/pharmaceutical vial 100 or the IV drip chamber tube 18.

Figure 11:
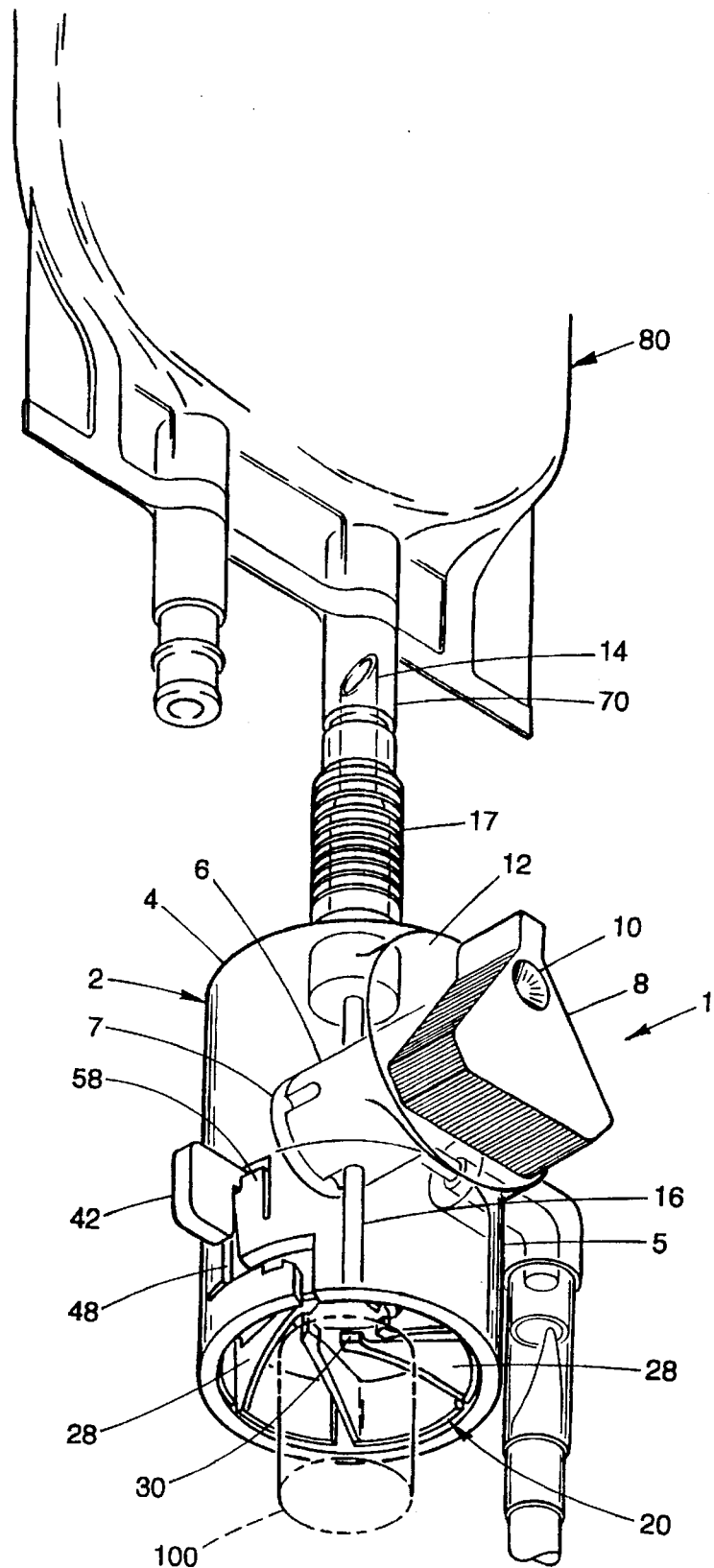
FIGS. 11 and 12 show the intravenous infusion system coupled to the IV bag with the mode selection knob rotated to a pharmaceutical mixing position so that the fluid contents of the IV bag can be mixed with the contents of a pharmaceutical vial.
Figure 12:
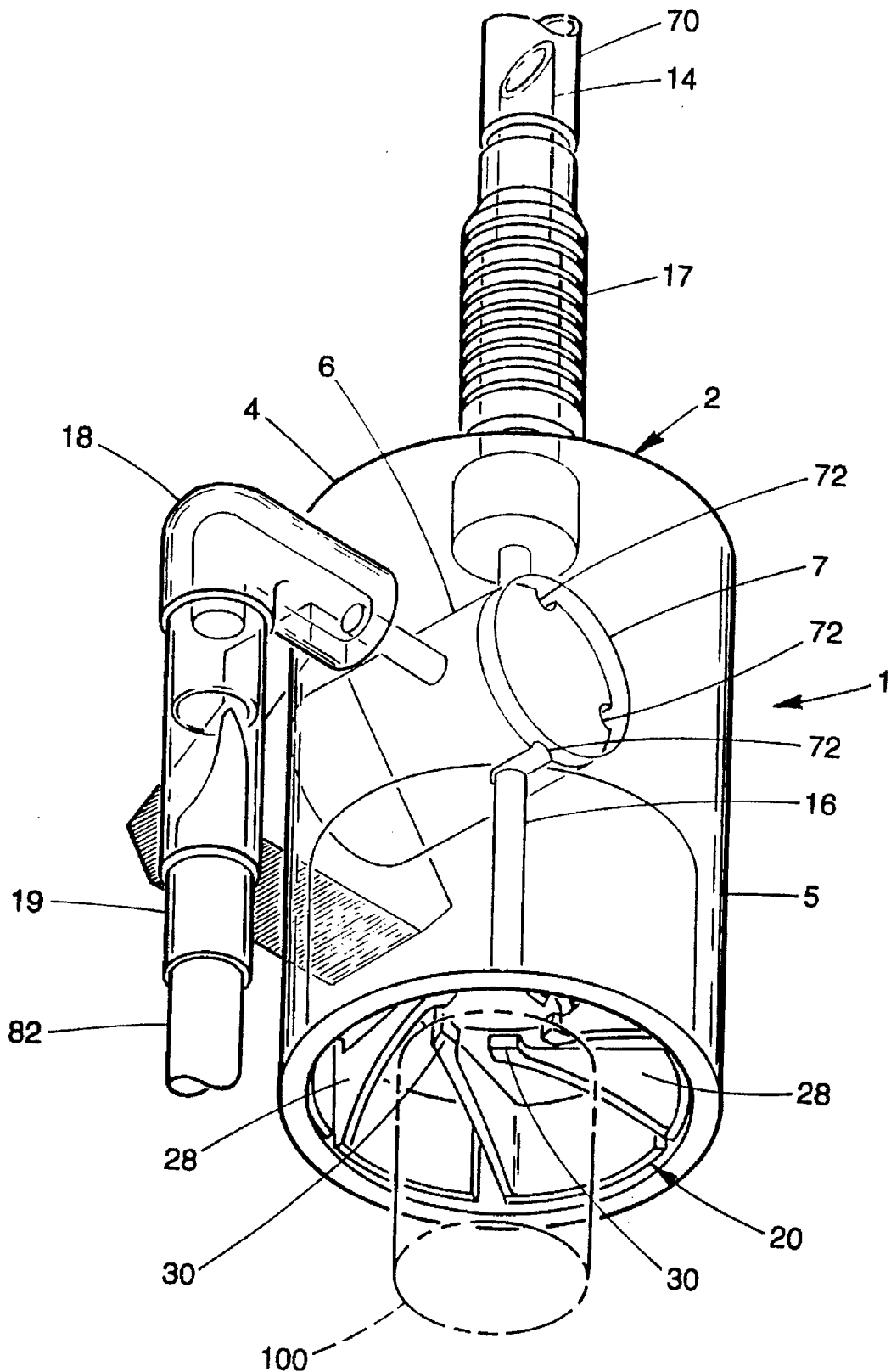

FIGS. 11 and 12 of the drawings show the generic infusion system 1 with the mode selection knob 8 rotated to the pharmaceutical mixing position. However, prior to the selection knob 8 being rotated to the pharmaceutical mixing position, the universal vial receiving and docking port 20 is first moved distally and completely through the two-stage docking port 5 of fluid control valve 2 to complete the second stage thereof. The foregoing is accomplished by the nurse manipulating the locking tab 42 of the vial limiting end cap 22 to move the neck 44 of locking tab 42 to the end of the track 48 in docking port 5. That is to say, and as was described when referring previously to FIG. 7, the neck 44 is first removed from the detent 54 and rotated circumferentially through timing slot 52 of docking port 5. Next, the locking tab 42 is pushed distally to cause the neck 44 thereof to ride through the bayonet slot 56, whereupon the neck 44 of locking tab 42 is captured by the recess 60 within lock catch 58 so as to lock the neck 44 at its distal-most point of travel through bayonet slot 56.

The aforementioned distal displacement of locking tab 42 causes the vial receiving and docking receptacle 20 and the medication/pharmaceutical vial 100 carried thereby to move from the proximal end to the distal end of docking port 5. Accordingly, the vial cannula 16 projecting from valve barrel 6 will pierce the septum of the vial 100 via the access opening 36 in end cap 22. The nurse then pulls the coupling sleeve 17 proximally along the administration port cannula 14 projecting from valve barrel 6. The coupling sleeve 17 will be compressed, whereby to expose the administration port cannula 14 to pierce the plastic barrier within the administration port 70 of IV bag 80. It may therefore be appreciated that the administration port cannula 14 communicates with the IV bag 80 and the vial cannula 16 communicates with the vial 100.

At this point, the nurse rotates the mode selection knob 8 from the left-most off position of FIGS. 8–10 to the longitudinally extending pharmaceutical mixing position of FIGS. 11 and 12. This rotation of selection knob 8 causes a corresponding rotation of the valve barrel 6 so that the fluid distribution paths 72 and the fluid collection chamber 7 thereof are now oriented to open a continuous fluid channel between the IV bag 80 and the medication/pharmaceutical vial 100 (best illustrated in FIG. 12). Accordingly, the fluid contents of the bag 80 are introduced to the fluid or dry contents of vial 100 under the influence of gravity. The nurse may wish to squeeze the IV bag 80 to accelerate the expulsion of the fluid from the bag 80 to vial 100 via administration port cannula 14, valve barrel 6 and vial cannula 16.

Once the contents of vial 100 have been uniformly and completely mixed with fluid from the IV bag 80, the nurse momentarily elevates the vial above the bag 80 so that the mixture of fluid and medication in vial 100 will return to the IV bag 80 by way of the fluid channel through the valve barrel 6 of fluid control valve 2.

Figure 13:
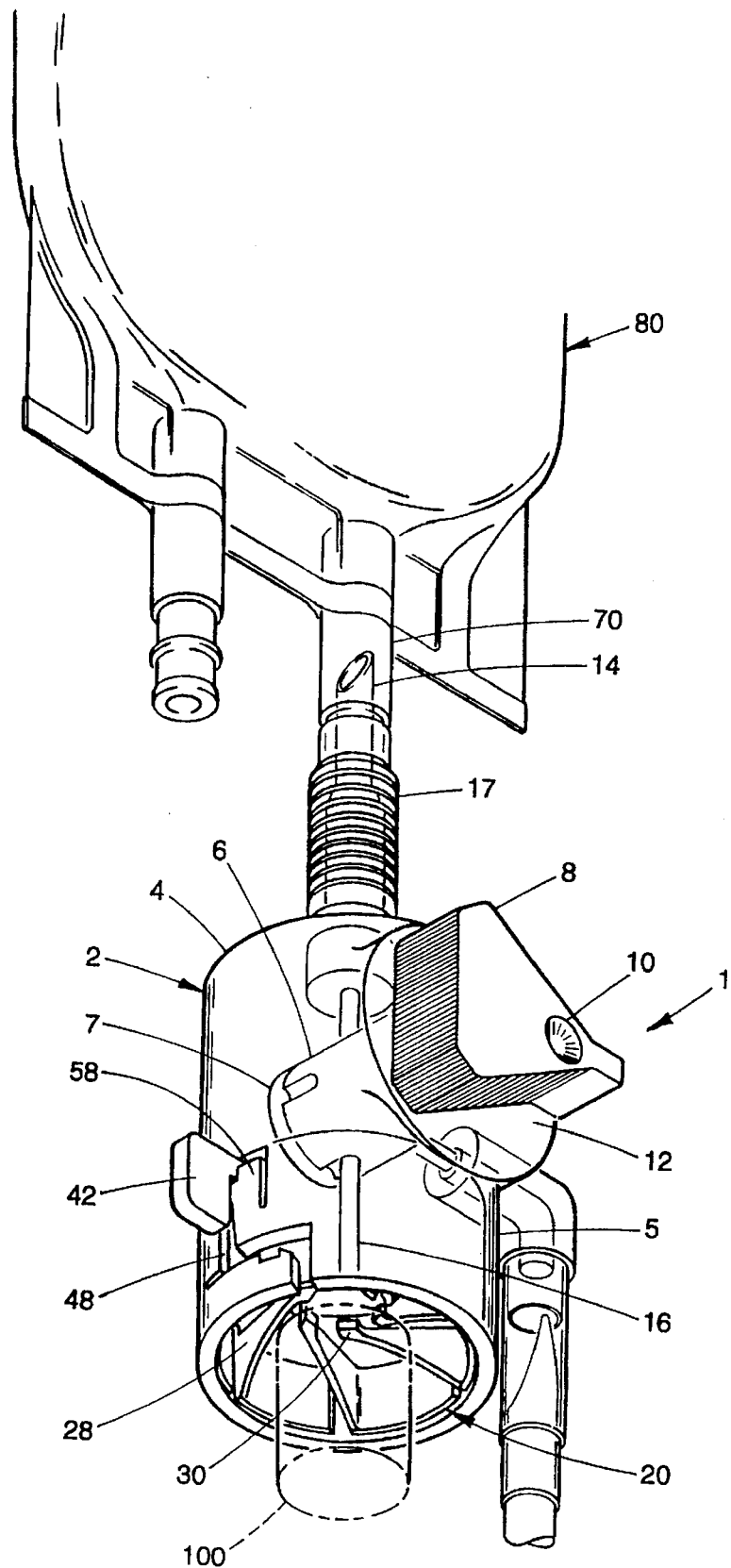
FIGS. 13 and 14 show the intravenous infusion system coupled to the IV bag with the mode selection knob rotated to the patient infusing position after the contents of the pharmaceutical vial and the IV bag are mixed together in solution so that the mixture can be administered from the IV bag to the patient by way of an IV fluid line.
Figure 14:
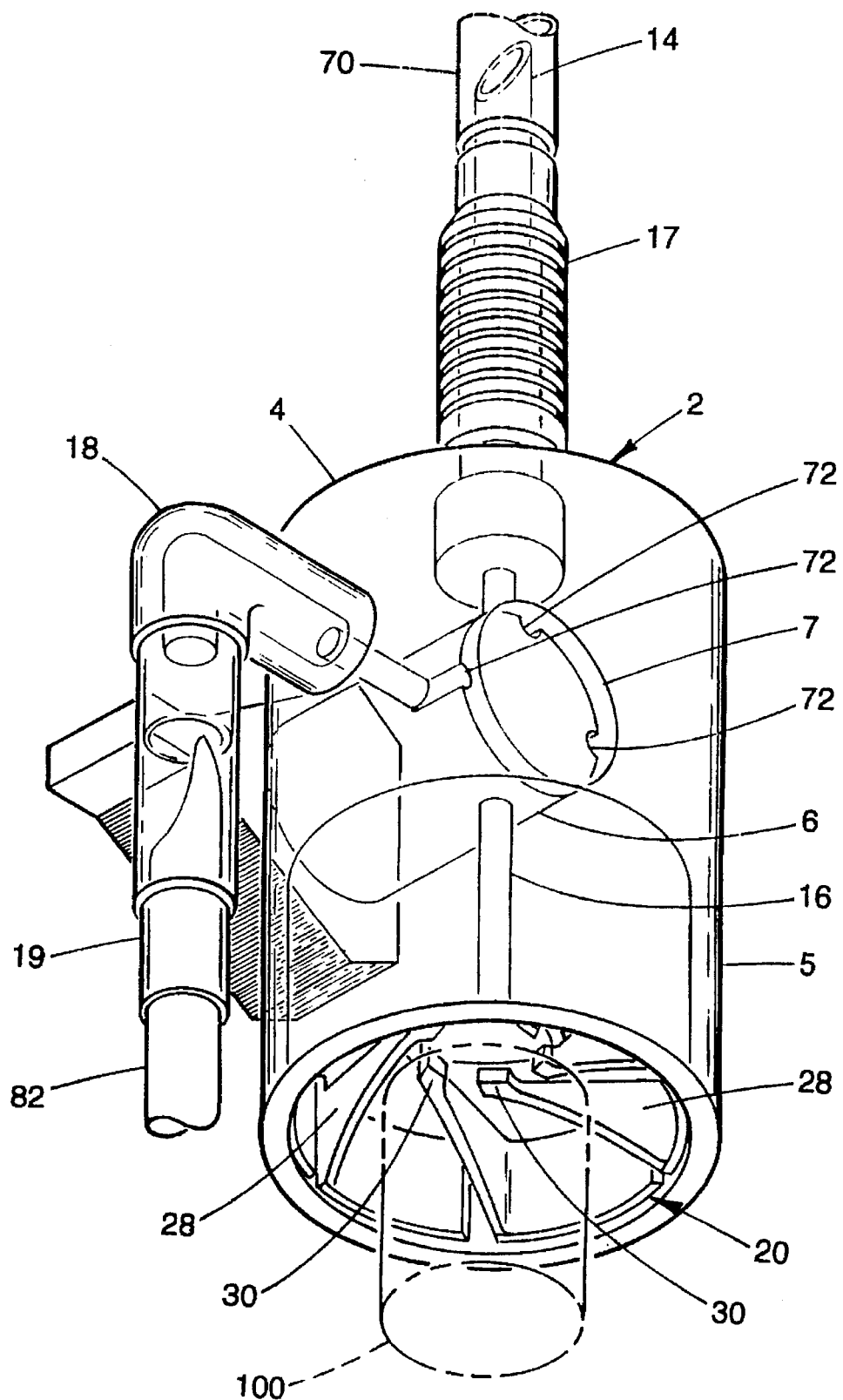

Finally, the nurse rotates the mode selection knob 8 from the pharmaceutical mixing position of FIGS. 11 and 12 to the right-most patient infusing position shown in FIGS. 13 and 14 of the drawings. This additional rotation of selection knob 8 causes an additional rotation of the valve barrel 6 so that the fluid distribution paths 72 and the fluid collection chamber 7 thereof are now oriented to open a continuous fluid channel between the IV bag 80 and the IV drip chamber tube 18 (best illustrated in FIG. 14). Accordingly, fluid from the IV bag 80, with the medication from vial 100 mixed in solution, can be delivered to the patient under the influence of gravity according to the patient's medical needs by way of administration port cannula 14, valve barrel 6, IV drip chamber tube 18 and an IV fluid line 82 attached to the fluid port 19 of tube 18.

After the IV has been concluded, the generic intravenous infusion system 1 and the IV bag 80 to which system 1 is connected are simply discarded. However, it may now be appreciated that any customized or generic liquid or powder medication stored in any proprietary or conventional medication/pharmaceutical vial can be efficiently, conveniently and completely mixed with the fluid contents of an IV bag so that the treatment of the patient can be tailored to his specific needs while reducing cost, inconvenience and the possibility of having to disclose confidential sales information to the manufacturers of such customized medication and/or proprietary vials. What is more, in order to maximize pharmaceutical life span, it may also be appreciated that the medication need not be exposed to the atmosphere or removed from the sealed vial in which it is stored until immediately prior to the administration of the IV.

It will be appreciated that while a preferred embodiment of the invention has been shown and described, various modifications and changes may be made without parting from the true spirit and scope of the invention.

Having thus set forth the preferred embodiment, what is claimed is:

1. An intravenous infusion system to be coupled to an IV bag in which a fluid is stored so that a medication stored in a pharmaceutical vial can be mixed with the fluid in the IV bag and the mixture administered to a patient from the IV bag by way of an IV fluid line, said infusion system comprising:

a fluid control valve including a housing and a valve barrel movably positioned within said housing and having a plurality of fluid distribution paths formed therein;

a first fluid channel extending through the housing of said fluid control valve from said valve barrel to be coupled to the IV bag;

a second fluid channel extending through the housing of said fluid control valve from said valve barrel to be coupled to the pharmaceutical vial in which the medication is stored;

a third fluid channel extending through the housing of said fluid control valve from said valve barrel to be coupled to the IV fluid line;

a vial receiving and docking receptacle to accept and carry said pharmaceutical vial;

means by which to move said vial receiving and docking receptacle relative to the housing of said fluid control valve from a first location at which said pharmaceutical vial carried by said vial receptacle is spaced from said second fluid channel to a second location at which said pharmaceutical vial is moved into fluid communication with said second fluid channel; and means by which to move said valve barrel within the housing of said fluid control valve to either block fluid communication or permit fluid communication via the fluid distribution paths of said valve barrel between the IV bag and one of said IV fluid line and said pharmaceutical vial carried by said vial receiving and docking receptacle depending upon the position to which said valve barrel is moved.

2. The intravenous infusion system recited in claim 1, wherein said first fluid channel is a hollow cannula having a first end extending from the valve barrel of said fluid control valve and a second end terminating at a sharp point adapted to penetrate the IV bag so as to place said IV bag in fluid communication via the fluid distribution paths of said valve barrel with one of said IV fluid line and said pharmaceutical vial depending upon the position to which said valve barrel is moved.

3. The intravenous infusion system recited in claim 1, wherein said second fluid channel is a hollow cannula having a first end extending from the valve barrel of said fluid control valve and a second end terminating at a sharp tip adapted to penetrate the septum of the pharmaceutical vial so as to place said IV bag in fluid communication via the fluid distribution paths of said valve barrel with said pharmaceutical vial depending upon the position to which said valve barrel is moved.

4. The intravenous infusion system recited in claim 1, wherein said vial receiving and docking receptacle includes an outer body and a plurality of flexible retaining arms projecting inwardly from said body for receiving and retaining the pharmaceutical vial to be carried by said vial receptacle.

5. The intravenous infusion system recited in claim 4, wherein each of said plurality of flexible retaining arms of said vial receiving and docking receptacle has a relatively wide finger located at one end thereof for engaging the pharmaceutical vial to be carried by said vial receiving and docking receptacle, said fingers causing said arms to bend in response to pushing forces applied to said fingers by said vial.

6. The intravenous infusion system recited in claim 1, wherein the housing of said fluid control valve has an open end to form a hollow docking port, said vial receiving and docking receptacle moving through said docking port from said first location at which said pharmaceutical vial carried by said vial receptacle is spaced from said second fluid channel to said second location at which said pharmaceutical vial communicates with said second fluid channel.

7. The intravenous infusion system recited in claim 6, further comprising a tab projecting from said vial receiving and docking receptacle, such that an axial pushing force applied to said tab causes a corresponding axial movement of said vial receptacle through the docking port in the housing of said fluid control valve from said first location to said second location.

8. The intravenous infusion system recited in claim 7, further comprising a guide track formed in the housing of said fluid control valve, the tab projecting from said vial receiving and docking receptacle riding through said guide track when said vial receptacle moves through the docking port in said housing from said first location to said second location.

9. The intravenous infusion system recited in claim 8, wherein said guide track has a detent formed therein, the tab projecting from said vial receiving and docking receptacle being captured by said detent when said vial receptacle is at said first location in said docking port to prevent the axial displacement of said vial receptacle through said docking port to said second location.

10. The intravenous infusion system recited in claim 8, wherein said guide track has a locking recess formed therein, the tab projecting from said vial receiving and docking receptacle being locked within said recess when said vial receptacle is moved through said docking port from said first location to said second location to prevent the axial relocation of said vial receptacle through said docking port from said second location to said first location.

11. The intravenous infusion system recited in claim 1, wherein said valve barrel is rotatable within said housing of said fluid control valve to either block fluid communication or permit fluid communication between the IV bag and one of said IV fluid line and said pharmaceutical vial via the fluid distribution paths in said valve barrel depending upon the position to which said valve barrel is rotated.

12. The intravenous infusion system recited in claim 11, further comprising a manually accessible mode selection knob connected to said valve barrel, said mode selection knob being rotated to cause a corresponding rotation of said valve barrel.

13. An intravenous infusion system to be coupled to an IV bag in which a fluid is stored so that a medication stored in a pharmaceutical vial can be mixed with the fluid in the IV bag and the mixture administered to a patient from the IV bag by way of an IV fluid line, said infusion system comprising:

a fluid control valve including a housing and a valve barrel movably positioned within said housing and having a plurality of fluid distribution paths formed therein;

fluid channel means to extend from the IV bag to each of the IV fluid line and the pharmaceutical vial in which the medication is stored by way of said fluid distribution paths of said valve barrel;

a vial receiving and docking receptacle including an outer body and a plurality of flexible retaining arms projecting inwardly from said outer body and adapted to receive and retain the pharmaceutical vial so that the pharmaceutical vial can be carded by said vial receiving and docking receptacle from a first location spaced from said fluid channel means to a second location coupled to and communicating with said fluid channel means; and means by which to move said valve barrel within the housing of said fluid control valve to either block fluid communication or permit fluid communication through said fluid channel means between the IV bag and one of the IV line and the pharmaceutical vial carried by said vial receiving and docking receptacle depending upon the position to which said valve barrel is moved.

14. The intravenous infusion system recited in claim 13, further comprising a hollow docking port surrounding at least some of said fluid channel means, said vial receiving and docking receptacle moving through said docking port from said first location at which said pharmaceutical vial carried by said vial receptacle is spaced from said fluid channel means to said second location at which said pharmaceutical vial is coupled to and communicates with said fluid channel means.

15. The intravenous infusion system recited in claim 14, further comprising a guide track formed in the housing of said fluid control valve and a tab projecting from said vial receiving and docking receptacle to be received in and ride through said guide track when said vial receiving and docking receptacle moves through the docking port in said housing from said first location to said second location.

16. The intravenous infusion system recited in claim 13, wherein each of said plurality of flexible retaining arms of said vial receiving and docking receptacle has a relatively wide finger located at one end thereof for engaging the pharmaceutical vial to be carried by said vial receiving and docking receptacle, said fingers causing said arms to bend in response to pushing forces applied to said fingers by the vial.

17. The intravenous infusion system recited in claim 13, wherein said fluid channel means include:

a first fluid channel extending through the housing of said fluid control valve from said valve barrel to be coupled to the IV bag;

a second fluid channel extending through the housing of said fluid control valve from said valve barrel to be coupled to the pharmaceutical vial in which the medication is stored; and a third fluid channel extending through the housing of said fluid control valve from said valve barrel to be coupled to the IV fluid line.

18. The intravenous infusion system recited in claim 17, wherein said first fluid channel is a hollow cannula having a first end extending from the valve barrel of said fluid control valve and a second end terminating at a sharp point adapted to penetrate the IV bag so as to place the IV bag in fluid communication via said plurality of fluid distribution paths of said valve barrel with one of the IV fluid line and the pharmaceutical vial depending upon the position to which said valve barrel is moved.

19. The intravenous infusion system recited in claim 17, wherein said second fluid channel is a hollow cannula having a first end extending from the valve barrel of said fluid control valve and a second end terminating at a sharp tip adapted to penetrate the septum of the pharmaceutical vial so as to place the IV bag in fluid communication via said plurality of fluid distribution paths of said valve barrel with the pharmaceutical vial depending upon the position to which said valve barrel is moved.

20. The intravenous infusion system recited in claim 13, wherein said valve barrel is rotatable within the housing of said fluid control valve to either block fluid communication or permit fluid communication between the IV bag and one of the IV fluid line and the pharmaceutical vial via said plurality of fluid distribution paths in said valve barrel depending upon the position to which said valve barrel is rotated.

* * * * *